United States Patent
Rastegar

(10) Patent No.: US 9,782,289 B1
(45) Date of Patent: Oct. 10, 2017

(54) SINUS PASSAGE EXPANSION DEVICE

(71) Applicant: Farhoud Z. Rastegar, San Diego, CA (US)

(72) Inventor: Farhoud Z. Rastegar, San Diego, CA (US)

( * ) Notice: Subject to any disclaimer, the term of this patent is extended or adjusted under 35 U.S.C. 154(b) by 334 days.

(21) Appl. No.: 14/628,774

(22) Filed: Feb. 23, 2015

Related U.S. Application Data

(60) Provisional application No. 61/968,591, filed on Mar. 21, 2014.

(51) Int. Cl.
    *A61M 29/00*     (2006.01)
    *A61F 5/56*     (2006.01)

(52) U.S. Cl.
    CPC ..................... *A61F 5/56* (2013.01)

(58) Field of Classification Search
    CPC ........ A61F 5/56; A61F 2005/563; A61F 5/08; A61F 2/186; A61F 2/18; A61B 17/24; A61B 2017/246; A61B 17/12104
    USPC ........................................................ 606/199
    See application file for complete search history.

(56) References Cited

U.S. PATENT DOCUMENTS

| | | |
|---|---|---|
| 5,752,510 A | 5/1998 | Goldstein |
| 6,244,265 B1 | 6/2001 | Cronk et al. |
| 6,270,512 B1 | 8/2001 | Rittmann |
| 8,047,201 B2 | 11/2011 | Guyuron et al. |
| 8,235,051 B2 | 8/2012 | Söderberg |
| 2004/0059368 A1 | 3/2004 | Maryanka |
| 2006/0085027 A1* | 4/2006 | Santin ............... A61F 5/08 606/199 |
| 2009/0272386 A1 | 11/2009 | Kurtz |
| 2009/0301499 A1 | 12/2009 | Chalk et al. |
| 2012/0325223 A1 | 12/2012 | Yamada et al. |

FOREIGN PATENT DOCUMENTS

WO     9851234 A3     12/1999

\* cited by examiner

*Primary Examiner* — Jonathan Miles
(74) *Attorney, Agent, or Firm* — Robert C. Montgomery; Montgomery Patent & Design, LP

(57) ABSTRACT

A sinus passage expansion device includes a pair of protruding tubular members connected to a base member. Each tubular member is split into hollow half portions each providing outwardly bulging forms which emulate an inner profile of a nasal cavity. The members are preferably made using a material having shape changing temperature sensitive properties. The base provides screen-covered apertures.

13 Claims, 6 Drawing Sheets

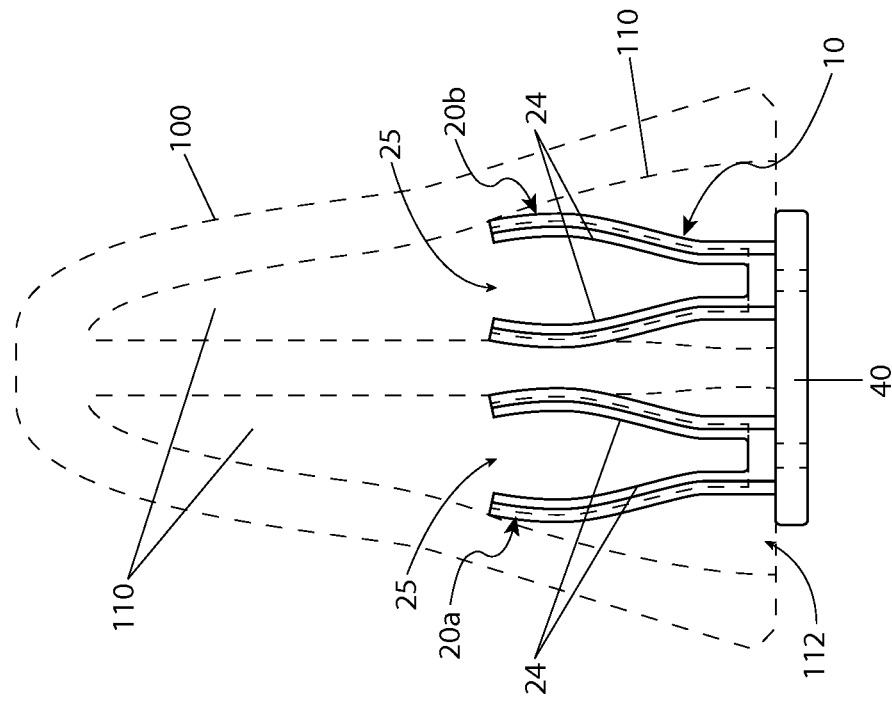
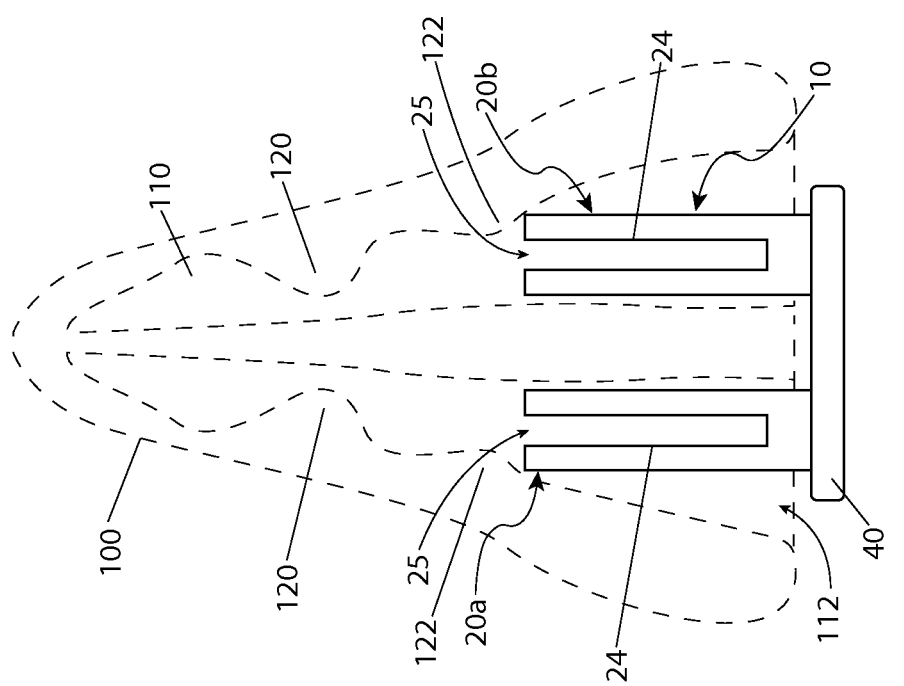

SINUS PASSAGE EXPANSION DEVICE

RELATED APPLICATIONS

The present invention was first described in and claims the benefit of U.S. Provisional Application No. 61/968,591, filed Mar. 21, 2014, the entire disclosures of which are incorporated herein by reference.

FIELD OF THE INVENTION

The present invention relates generally to an expansion device configured to be insertable into nasal cavities to expand the sinuses in order to reduce the occurrence of snoring.

BACKGROUND OF THE INVENTION

People that suffer from asthma, allergies, or sinus problems know all too well of the difficulties that they face in trying to get a good night's sleep. Oftentimes, when these people sleep, their nasal passages may become blocked due to swelling thereby making it difficult to breathe. This breathing difficulty frequently results in periodic disruptions of sound sleep. The blockage of nasal passages may also lead to snoring. Therefore, a variety of products have been developed, ranging from inhalers and medicines, to adhesive strips that are applied across the outer surface of the nose, that are intended to relieve these symptoms. However, all of these products suffer from inherent shortcomings. Inhalers and medicines are time dependant and do not tend to last throughout the desired period of sleep. Adhesive strips can irritate the skin and do not open nasal passages as fully. Surgery is another option, but carries inherent risks and other complications and thus is typically the solution of last resort. Accordingly, there exists a need for a means by which air flow through the nose and nasal cavities can be optimized, without the disadvantages of the aforementioned commonly available treatments. The use of the expansion device apparatus provides enhanced breathing ability which facilities sound and uninterrupted sleep while reducing snoring, in a manner which is quick, easy, effective, non-pharmacological and most importantly, safe.

SUMMARY OF THE INVENTION

The inventors have recognized the aforementioned issues and inherent problems and observed that there is a lack in the prior art for a means to efficiently and safely expand a nasal sinuses.

It is therefore an object of the invention to provide an expansion device including a pair of cylindrical tubular structures with an open top and curved shape. Each tubular structure has a slit longitudinally running along the length of the tube and a cylindrical mounting ring which is connected to its bottom end. Each mounting ring is connected to a planar base. Each tubular structure has a transformation temperature at which point the device changes shape. The length of the longitudinal slit does not equal or exceed that of the tubular structures.

The tubular structures are each composed of a nickel-titanium alloy or other composite materials having temperature sensitive shape memory properties to that of a nickel-titanium alloy. Each tubular structure is configured to emulate an internal profile of a nasal cavity when at or above the transformation temperature and configured to maintain a tubular profile when below the transformation temperature.

The tubular structures are adhered to the cylindrical mounting rings which are likewise adhered to the planar base. The planar base is made of a semi-rigid plastic material. The planar base has at least one base aperture covered by a screen mesh.

An expansion limiting ring provides a tensile force against an upper intermediate portion of each tubular structure. The expansion limiting ring is comprised of rubber, latex, or a similar elastic material. The expansion limiting ring is sized to provide proportional expansion resistance to said tubular structures.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 5a is an environmental view of the sinus passage expansion device 10 depicting insertion into a user's 100 nasal cavity 110 while in a deformed and collapsed state, according to a preferred embodiment of the present invention;

FIG. 5b is an environmental view of the sinus passage expansion device 10 depicting an installed in-use state within the user's 100 nasal cavity 110, according to a preferred embodiment of the present invention; and, FIG. 6 is a perspective view of the sinus passage expansion device 10 depicting utilization of optional expansion limiting rings 50, according to an alternate embodiment of the present invention.

Figure 1:
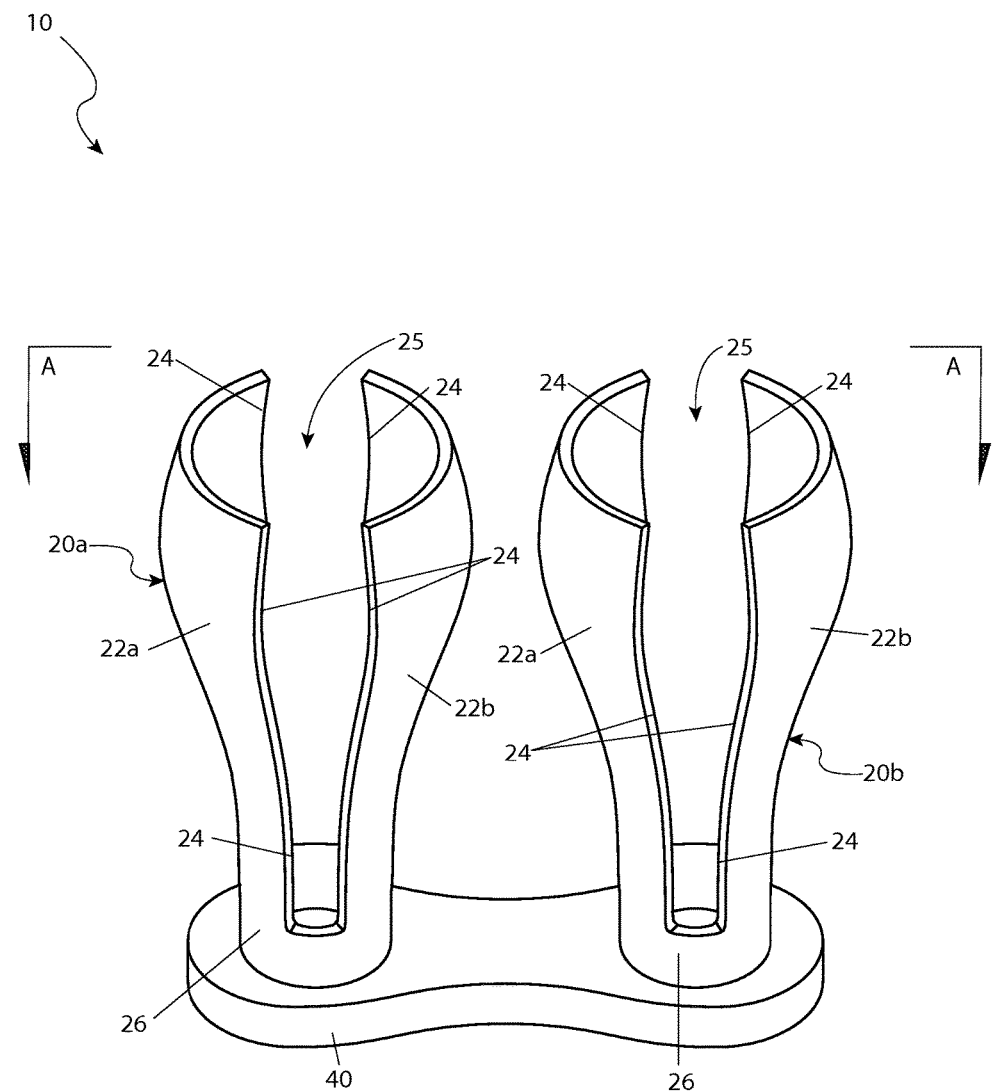
FIG. 1 is an upper perspective view of a sinus passage expansion device 10, according to a preferred embodiment of the present invention.

DESCRIPTIVE KEY 10 sinus passage expansion device
20a first tubular structure
20b second tubular structure
22a first half-tube
22b second half-tube
24 slit
25 opening
26 mounting ring
40 base
42 base aperture
44 screen mesh
50 expansion limiting ring
100 user/nose
110 nasal cavity
112 nostril opening
120 superior concha
122 inferior concha

DETAILED DESCRIPTION OF THE PREFERRED EMBODIMENT

Figure 6:
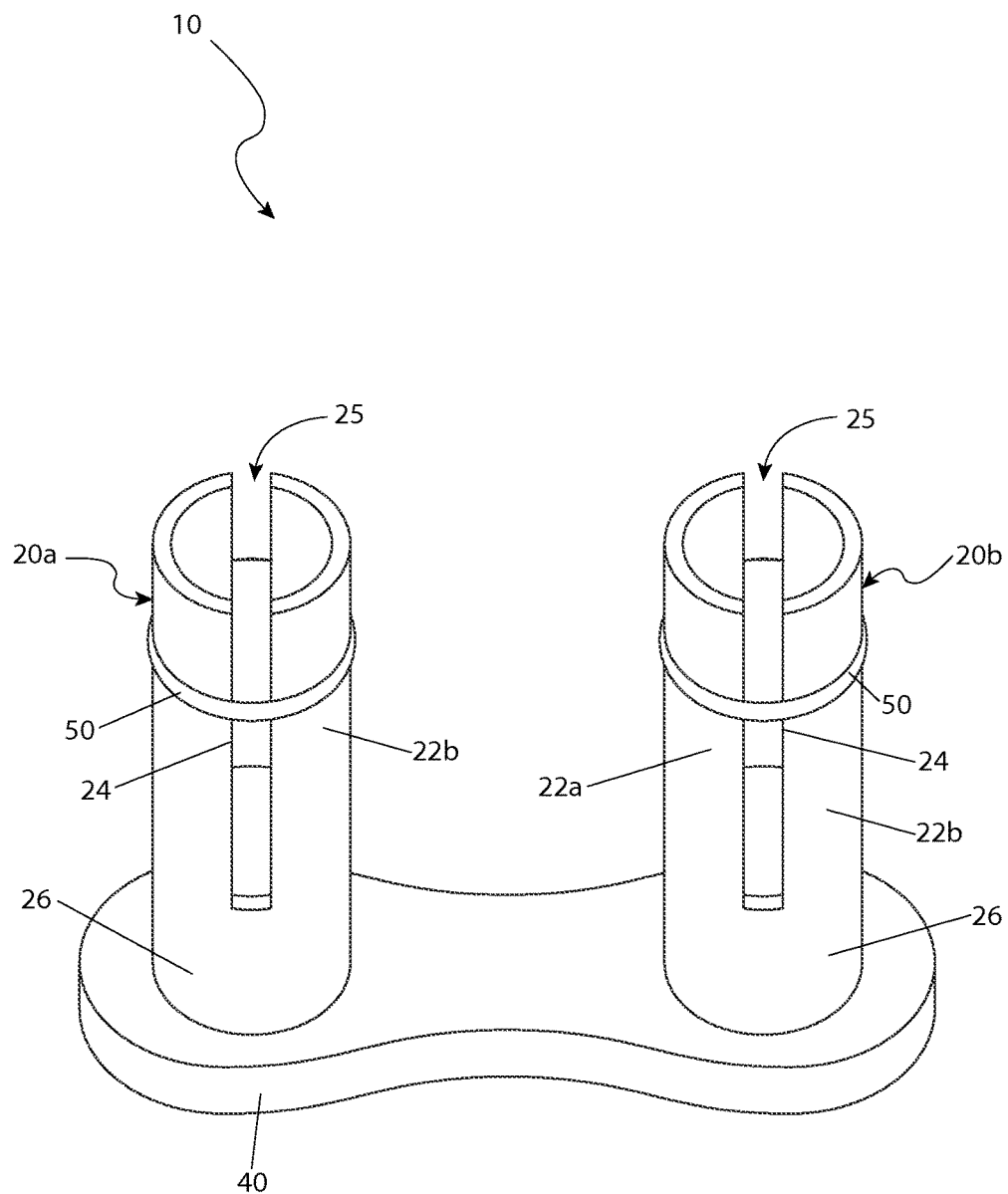

The best mode for carrying out the invention is presented in terms of its preferred embodiment, herein depicted within FIGS. 1 through 5b, and in terms of an alternate embodiment, herein depicted in FIG. 6. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a sinus passage expansion device (herein described as the "device") 10, which provides a device designed to improve nighttime breathing, and reduce snoring by internally expanding a user's nasal cavity 110, thereby increasing air flow.

Figure 2:
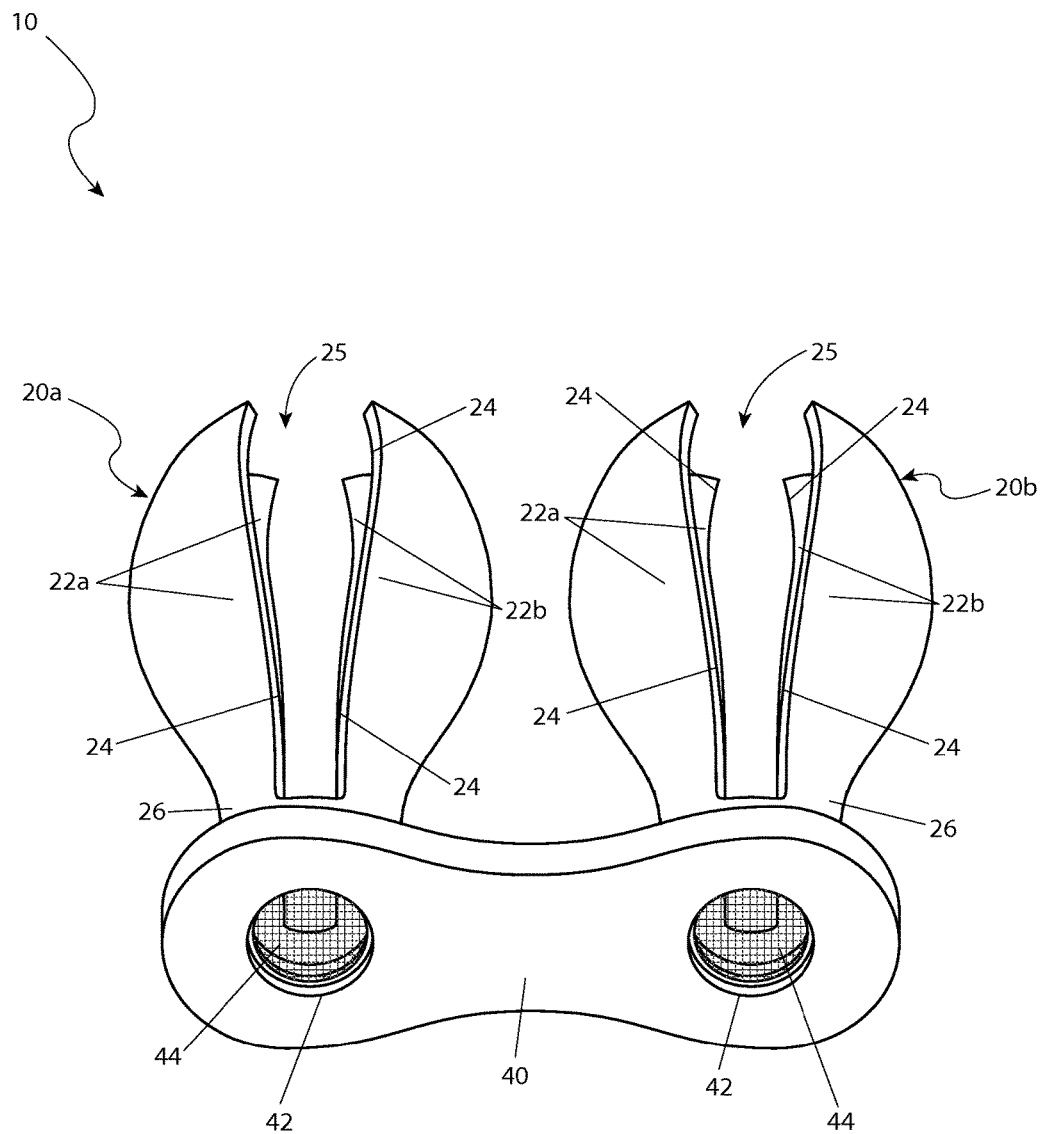
FIG. 2 is a bottom perspective view of the sinus passage expansion device 10, according to a preferred embodiment of the present invention.
Figure 3:
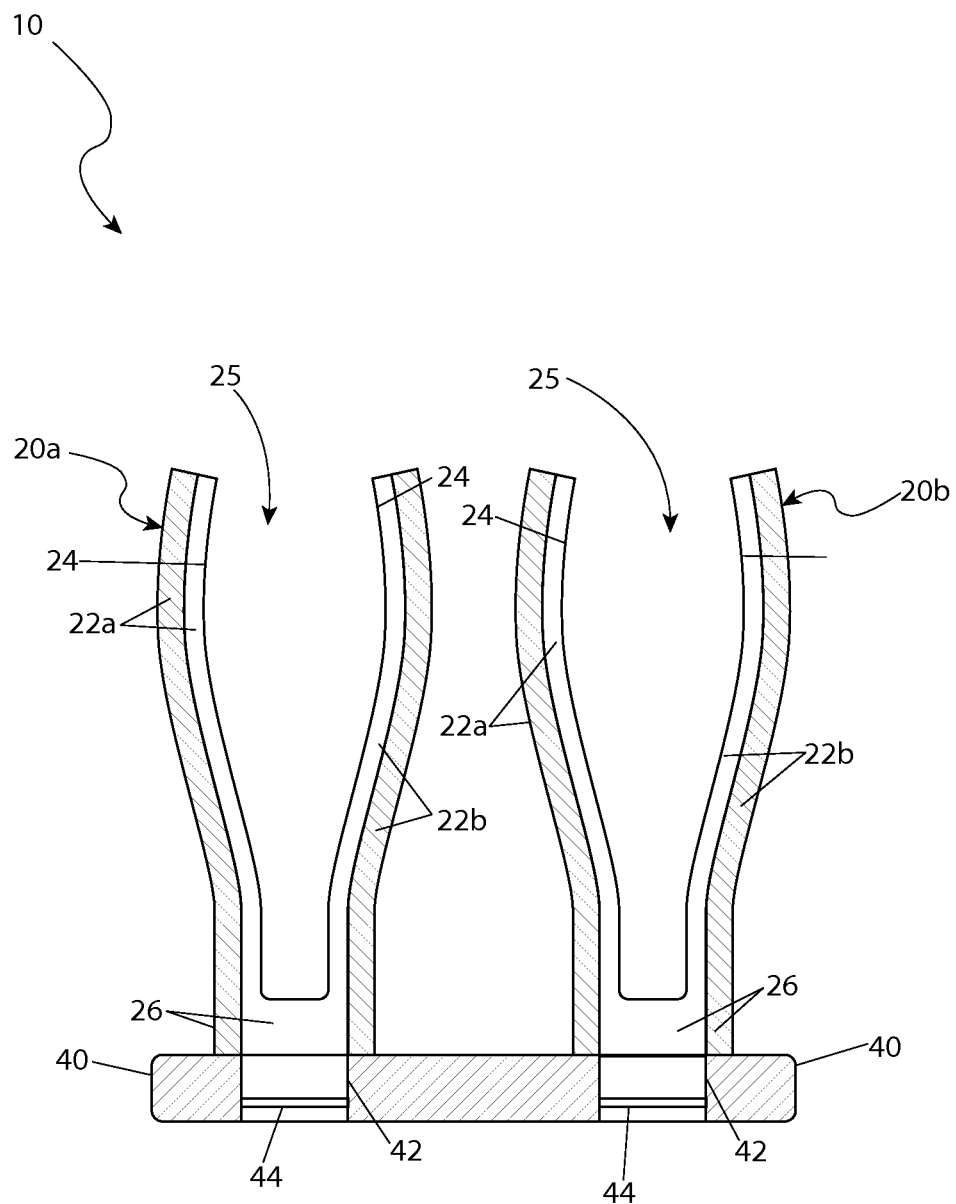
FIG. 3 is a sectional view of the sinus passage expansion device 10 taken along section line A-A (see FIG. 1), according to a preferred embodiment of the present invention.

Referring now to FIGS. 1, 2, and 3, perspective and sectional views of the device 10, according to the preferred embodiment of the present invention, are disclosed. The device 10 includes of a pair of cylindrical tubular structures 20a, 20b having a top opening 25 and a curved shape which emulates an internal profile of a normal nasal cavity 110. The tubular structures 20a, 20b are arranged in a vertical parallel manner, each being split into mirror-image first half tube 22a and second half tube 22b portions which are separated by a vertical slits 24 which extend down both side surfaces of each tubular structure 20a, 20b. The tubular structures 20a, 20b are preferably made of a nickel-titanium alloy, or other composite material having similar expansion properties, which provides specific temperature sensitive physical properties which cause the tubular structures 20a, 20b to expand when inserted into a user's nasal cavity 110 to provide enhanced breathing capability (also see FIGS. 4, 5a, and 5b).

The first half-tube 22a and second half-tube 22b portions are separated by the slit 24 from a top edge downward, and are joined together at a bottom end by an integral cylindrical mounting ring portion 26. The mounting ring portions 26 of each tubular structure 20a, 20b are mounted adjacent to each other, and to a subjacent planar base 40 using adhesives or other equivalent methods of attachment. The base 40 provides a generally oval-shaped platform envisioned to be made of a semi-rigid plastic material. The base 40 covers over a user's nostril openings 112 and includes a pair of integral circular base apertures 42 which enable air to flow through. Each base aperture 42 is aligned with a respective mounting ring 26 and covered by a circular screen mesh portion 44. The screen mesh 44 provides sufficient open area to enable normal breathing through the tubular structures 20a, 20b.

Figure 4:
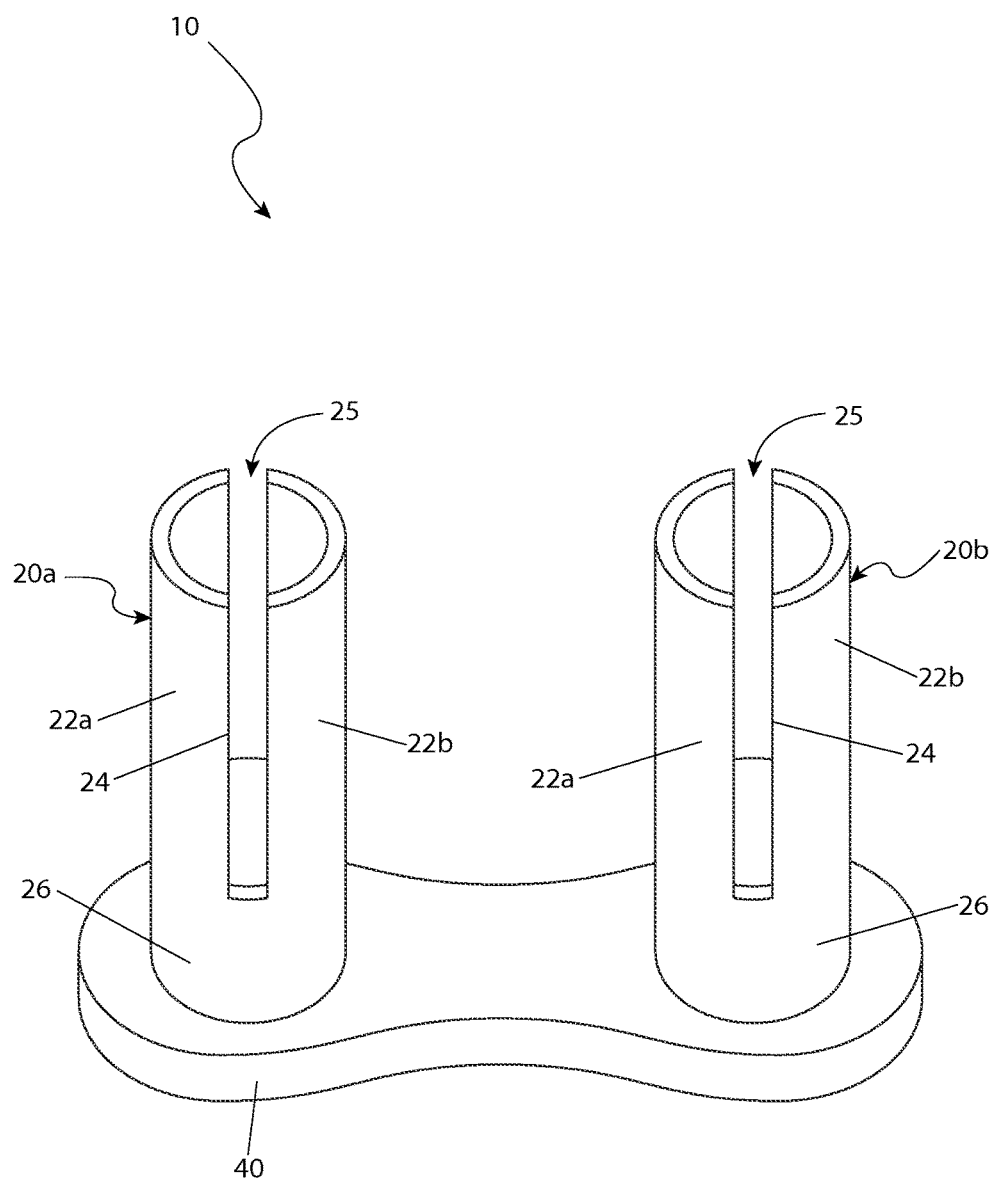
FIG. 4 is a perspective view of the sinus passage expansion device 10 depicting a deformed and collapsed state, according to a preferred embodiment of the present invention.

Referring now to FIG. 4, a perspective view of the device 10 depicting a deformed and collapsed state, according to a preferred embodiment of the present invention, is disclosed. The tubular structure portions 20a, 20b of the device 10 are made using a nickel-titanium alloy material to produce temperature sensitive malleability and expanding properties. When the nickel-titanium alloy is placed within a cool temperature, the alloy becomes temporarily pliable and flexible. As the nickel-titanium alloy is exposed to a higher body temperature, the alloy expands and retains its original shape, and returns to its original hardness. The expansion properties of the nickel-titanium alloy are controlled by creating a particular original form as well as changing the thickness of the material. Although the preferred material for the tubular structure portions 20a, 20b is nickel-titanium alloy, other composite materials having similar expansion properties may be utilized, and as such should not be interpreted as a limiting factor of the device 10.

The device 10 is prepared for use by being placed within a refrigerator or other cooling means resulting in a softening of the nickel-titanium alloy, thereby allowing for temporary manipulation of the tubular structures 20a, 20b into a narrowed collapsed state by pressing the half-tube portions 22a, 22b together and reducing a width of the slits 24.

When placed onto the nasal cavity portion 110 of a user's nose 100, the expanding properties of the nickel-titanium alloy, or other composite material having similar expansion properties, causes the previously collapsed half-tubes 22a, 22b to expand, thereby separating from each other and then becoming rigid. This expansion of each tubular structure 20a, 20b opens up the nasal cavity 110, and provides a sufficient amount of air to pass through for proper breathing.

Referring now to FIGS. 5a and 5b, environmental views of the device 10 depicting insertion and installation within a user's 100 nasal cavity 110, according to a preferred embodiment of the present invention, is disclosed. The device 10 is cooled and pressed into a narrowed collapsed state by pressing the half-tube portions 22a, 22b together. In this state the tubular structures 20a, 20b are easily inserted upwardly into the user's 100 nasal cavity 110.

As the user's 100 body temperature warms the device 10, the properties of the nickel-titanium alloy causes the tubular structures 20a, 20b to expand and return to their original split and outwardly curving shape, thereby pressing against and expanding internal superior concha 120 and inferior concha 122 tissues within the nasal cavity 110.

Removal of the device 10 is accomplished by pulling downwardly upon the base 40 and extracting the tubular structures 20a, 20b from the nasal cavity 110. The device 10 may then be cleaned for subsequent repeated use.

Referring now to FIG. 6, a perspective view of the device 10 depicting utilization of optional expansion limiting rings 50, according to an alternate embodiment of the present invention. The expansion limiting rings 50 help control a diameter of the tubular structures 20a, 20b when expanded.

The device 10 is illustrated here having expansion limiting rings 50 installed upon respective tubular structures 20a, 20b. The expansion limiting rings 50 provide circular elastic bands which are in tension around an upper intermediate portion of each tubular structure 20a, 20b. The expansion limiting rings 50 are envisioned to be made using rubber, latex, or a similar elastic material. During expansion of the tubular structures 20a, 20b within the nasal cavity 110, the expansion limiting rings 50 provide proportional resistance as the tubular structures 20a, 20b are heated. Therefore, the expansion limiting rings 50 provide additional control of the fit and feel of the device 10 within the nasal cavity 110.

It is understood that different models of the expansion limiting rings 50 may be introduced by varying the material and/or cross-sectional area of the expansion limiting rings 50 to provide a desired tensile resistance, and a corresponding diameter of each tubular structure 20a, 20b.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the device 10, it would be installed as indicated in FIGS. 5a and 5b.

The method of installing and utilizing the device 10 may be achieved by performing the following steps: procuring the device 10; placing the device 10 within a refrigerator or other cooling means allowing the tubular structures 20a, 20b to soften; collapsing the tubular structures 20a, 20b in a temporary manner by pressing the half-tube portions 22a, 22b together and reducing a width of the slits 24; inserting the tubular structures 20a, 20b upwardly into the user's 100 nasal cavity 110 in a coincidental manner until the base 40 covers the nostril openings 112; allowing the half-tube portions 22a, 22b to be warmed by the user's 100 body temperature; allowing the half-tube portions 22a, 22b to expand, separate, and return to their original split and outwardly curving shape; allowing the tubular structures 20a, 20b to press against and expand internal superior concha 120 and inferior concha 122 tissues within the nasal cavity 110; and, enabling increased airflow through a user's 100 nasal cavity 110, thereby improving nighttime breathing while also reducing snoring, afforded a user of the person's invention 10.

The method of installing and utilizing the optional expansion limiting rings 50 upon the device 10 may be achieved by performing the following additional steps: inserting each tubular structure 20a, 20b through a respective expansion limiting ring 50; positioning each expansion limiting ring 50 at an upper intermediate portion of each tubular structure 20a, 20b; allowing the expansion limiting rings 50 to provide proportional resistance to the tubular structures 20a, 20b as they are heated within the nasal cavity 110; and, allowing the expansion limiting rings 50 to provide additional control of an expanded diameter of the tubular structures 20a, 20b, and correspondingly, the fit and feel of the device 10 during use.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. An expansion device, comprising:
   a pair of cylindrical tubular structures, each having a top opening and a curved shape, a slit longitudinally disposed along a length and extending to an end thereof, and a cylindrical mounting ring connected to a bottom end thereof;
   an expansion limiting ring providing a tensile force against an upper intermediate portion of each tubular structure;
   a planar base connected to each mounting ring, and,
   having a transformation temperature at which point said device is formable;
   wherein slit enables said pair of tubular structures to splay open when expanded.

2. The device of claim 1, wherein a length of said longitudinal slit does not equal or exceed that of said tubular structures.

3. The device of claim 1, wherein said pair of tubular structures each further comprise a nickel-titanium alloy.

4. The device of claim 1, wherein said pair of tubular structures each further comprise any composite material having similar temperature sensitive shape memory properties to that of nickel-titanium alloy.

5. The device of claim 4, wherein each tubular structure is configured to emulate an internal profile of a nasal cavity when at or above said transformation temperature.

6. The device of claim 4, wherein each tubular structure is configured to maintain a tubular profile when below said transformation temperature.

7. The device of claim 1, wherein said tubular structures are adhered to said cylindrical mounting rings.

8. The device of claim 1, wherein said cylindrical mounting rings are adhered to said planar base.

9. The device of claim 1, wherein said base comprises a semi-rigid plastic material.

10. The device of claim 1, wherein said base comprises at least one base aperture.

11. The device of claim 1, further comprising a screen mesh covering each base aperture.

12. The device of claim 1, wherein each expansion limiting ring is comprised of rubber, latex, or a similar elastic material.

13. The device of claim 1, wherein each expansion limiting ring is sized to provide proportional expansion resistance to said tubular structures.

* * * * *